United States Patent [19]

Ishikawa et al.

[11] Patent Number: 4,517,189
[45] Date of Patent: May 14, 1985

[54] 2,6,7,8-SUBSTITUTED QUINAZOLINES, PROCESS FOR PRODUCTION THEREOF, AND USE THEREOF

[75] Inventors: Masayuki Ishikawa, Tokyo; Hiroshi Azuma, Asaka; Akiko Sugimoto, Hino; Noriko Takahashi, Tokyo; Yoshimi Takashima, Akishima, all of Japan

[73] Assignee: Showa Denko K.K., Tokyo, Japan

[21] Appl. No.: 519,235

[22] Filed: Aug. 2, 1983

[51] Int. Cl.³ .................. A61K 31/505; C79D 239/74
[52] U.S. Cl. .................................... 514/259; 544/283
[58] Field of Search .................... 544/283; 424/251

[56] References Cited

U.S. PATENT DOCUMENTS 3,637,693 1/1972 Otterstedt et al. .................. 544/283

FOREIGN PATENT DOCUMENTS 1074047 1/1960 Fed. Rep. of Germany ...... 544/283

*Primary Examiner*—Glennon H. Hollrah
*Assistant Examiner*—James H. Turnipseed
*Attorney, Agent, or Firm*—Sherman & Shalloway

[57] ABSTRACT

A 2,6,7,8-substituted quinazoline represented by the following formula

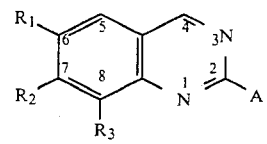

wherein $R_1$ and $R_3$ each represent a lower alkyl group, $R_2$ represents a lower alkoxy-carbonyl group, and A represents a lower alkyl group, or a phenyl or benzyl group which is unsubstituted or substituted by a substituent selected from the class consisting of halogen atoms, a trifluoromethyl group and lower alkyl groups, or its acid addition salt. The said compound can be prepared by reacting a compound represented by the following formula

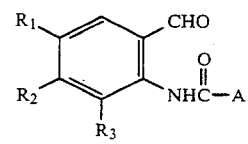

wherein $R_1$, $R_2$, $R_3$ and A are as defined, with ammonia. A pharmaceutical composition comprising the said compound as an active ingredient is useful for the treatment of disorders of the circulatory system.

10 Claims, No Drawings

2,6,7,8-SUBSTITUTED QUINAZOLINES, PROCESS FOR PRODUCTION THEREOF, AND USE THEREOF

This invention relates to novel compounds not described in the literature, and a pharmaceutical composition containing such as novel compound as an active ingredient.

More specifically, this invention relates to a 2,6,7,8-substituted quinazoline represented by the following formula

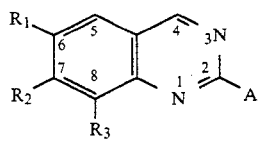

(I)

wherein $R_1$ and $R_3$ each represent a lower alkyl group, $R_2$ represents a lower alkoxycarbonyl group, and A represents a lower alkyl group, or a phenyl or benzyl group which is unsubstituted or substituted by a substituent selected from the class consisting of halogen atoms, a trifluoromethyl group and lower alkyl groups, and its acid addition salt.

The invention also pertains to a process for producing the compound of formula (I), and a pharmaceutical composition comprising the compound of formula (I) as an active ingredient.

The present inventors have made investigations about the development of quinazoline derivatives useful as medicines, and finally succeeded in synthesizing the 2,6,7,8-substituted quinazolines of formula (I) and the acid addition salts thereof. They have also found that the compound of formula (I) and the acid addition salts thereof are novel compounds not described in the literature, and are useful compounds for the prevention and treatment of disorders of the circulatory system which exhibit platelet aggregation inhibiting activity and vasodilating activity.

It is an object of this invention therefore to provide novel compounds of formula (I) and acid addition salts thereof.

Another object of this invention is to provide a process for producing the compounds of formula (I) and acid addition salts thereof.

Still another object of this invention is to provide a pharmaceutical composition comprising the compound of formula (I) or its pharmaceutically acceptable acid addition salt which is useful for the treatment of the circulatory disorders of the circulatory system.

The above and other objects and advantages of this invention will become more apparent from the following description.

The compounds of formula (I) of this invention can be produced by the action of ammonia on a compound of the following formula (II)

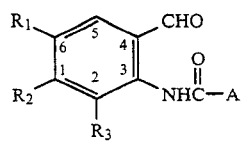

(II)

wherein $R_1$ and $R_3$ each represent a lower alkyl group, $R_2$ represents a lower alkoxy-carbonyl group, and A represents a phenyl or benzyl group which is unsubstituted or substituted by a substituent selected from the class consisting of halogen atoms, a trifluoromethyl group and lower alkyl groups.

The compound of formula (II) can be produced, for example, from a methyl 2-amino-4-lower alkoxycarbonyl-3,5-di-lower alkylbenzoate of the following formula (IV) by the process schematically shown below ($R_1$, $R_2$, $R_3$ and A are as defined above).

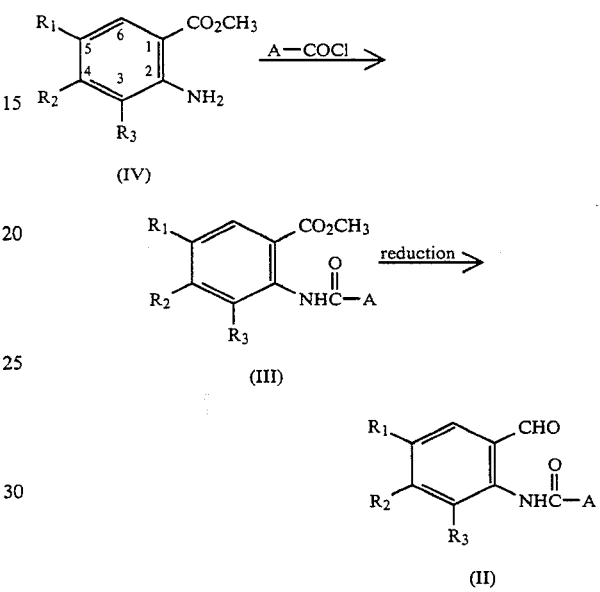

The compound of formula (IV) can be produced by a method known per se, for example by the esterification of the Hoffmann rearrangement reaction product of a 4-lower alkoxycarbonyl-3,5-di-lower-alkyl phthalimide (see, Eguchi and Ishikawa, Report of the Institute for Medical and Dental Engineering, Tokyo Medical and Dental University, Vol. 11, page 55, 1977).

The reaction of the compound of formula (IV) with a compound of formula A—COCl (wherein A is as defined above) can be carried out, for example, as follows: The compound of formula (IV) is dissolved in as inert solvent such as chloroform, and an acid binder such as triethylamine is added. With stirring, an acid chloride of the formula A—COCl is added dropwise, and the mixture is reacted at room temperature to the refluxing temperature of the solvent used for a period of, for example, 3 to 24 hours. The reaction mixture is washed with an aqueous alkali, and dried, and subjected to such operations as solvent evaporation and recrystallization to give the compound of formula (IV).

The compound of formula (II) can be easily produced by reducing the compound of formula (III) which can be formed as above. The reducing reaction can be performed, for example, in the following manner. The compound of formula (III) is dissolved in an inert solvent such as dry benzene, and a solution of Vitride in an inert solvent such as benzene is added dropwise at room temperature with stirring, and the mixture is reacted for a period of, for example, 1 to 5 hours. The reaction mixture is washed with dilute sulfuric acid, and dried. The solvent is evaporated, and the residue is again dissolved in such an inert solvent as dichloromethane, and reacted with manganese dioxide at room temperature with stirring for a period of, for example, 3 to 24 hours. The reaction mixture is filtered, and subjected to such treatments as solvent evaporation and recrystallization to give the compound of formula (II).

The compound of formula (I) can be easily produced by the action of ammonia on the compound of formula (II) which can be obtained in the above manner.

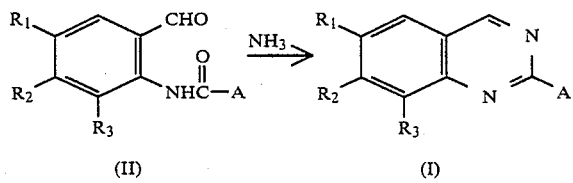

According to one preferred embodiment of reacting the compound of formula (II) with ammonia, ethanol saturated with ammonia gas while cold is prepared, and the compound of formula (II) is dissolved in it. The amount of ethanol saturated with ammonia can be properly chosen, and is, for example, about 10 to about 100 parts by volume per part by weight of the compound of formula (II).

The reaction proceeds at room temperature, and cooling or heating is not particularly necessary. After a solution of the compound of formula (II) is left to stand in ethanol saturated with ammonia gas at room temperature for 10 hours to several days, the solvent is evaporated. The residue is purified by such a purifying procedure as recrystallization or column chromatography to give the compound of formula (I).

The reaction temperature is, for example, about 5° to about 50° C.

Examples of the compound of formula (II) used in the reaction include methyl, ethyl, propyl, isopropyl, butyl and isobutyl esters of 3-acetylamino-4-formyl-2,6-dimethylbenzoic acid, methyl, ethyl, propyl, isopropyl, butyl and isobutyl esters of 4-formyl-2,6-dimethyl-3-phenylacetylaminobenzoic acid, methyl, ethyl, propyl, isopropyl, butyl and isobutyl esters of 3-benzoylamino-4-formyl-2,6-dimethylbenzoic acid, methyl, ethyl, propyl, isopropyl, butyl and isobutyl esters of 3-[o-, m- or p-chloro(or fluoro)benzoylamino]-4-formyl-2,6-dimethylbenzoic acid, methyl, ethyl, propyl, isopropyl, butyl and isobutyl esters of 4-formyl-2,6-dimethyl-3-(o, m- or p-trifluoromethylbenzoylamino)benzoic acid, and methyl, ethyl, propyl, isopropyl, butyl and isobutyl esters of 4-formyl-2,6-dimethyl-3-(o-, m- or p-tolylamino)benzoic acid.

Preferred examples of $R_1$ and $R_3$ in the compound of formula (I) are lower alkyl groups having 1 to 3 carbon atoms, especially a methyl group, and examples of $R_2$ are lower alkoxy-carbonyl groups with the alkyl moiety having 1 to 3 carbon atoms, such as an ethoxycarbonyl group. Preferred examples of A in formula (I) are lower alkyl groups having 1 to 3 carbon atoms such as a methyl group, and a phenyl or benzyl group with is unsubstituted or substituted by a substituent selected from the class consisting of halogen atoms such as Cl or F, a trifluoromethyl group and lower alkyl groups having 1 to 3 carbon atoms such as a methyl group.

The compounds of formula (I) of this invention may be in the form of their acid addition salts, preferably their pharmaceutically acceptable acid addition salts.

These acid addition salts can be easily prepared by contacting the compounds of formula (I) with organic or inorganic acids. Examples of the acids are mineral acids such as hydrochloric acid, sulfuric acid and hydrobromic acid, and organic acids such as oxalic acid, maleic acid and malic acid.

The compounds of formula (I) and their pharmaceutically acceptable acid addition salts in accordance with this invention exhibit platelet aggregation inhibiting activity and vasodilating activity, and are useful for the prevention and treatment of disorders of the circulatory system.

For example, the compounds of formula (I) and their pharmaceutically acceptable acid addition salts strongly inhibit platelet aggregation induced by arachidonic acid in an aggregation test of plasma having platelets suspended therein which has been drawn from rabbits.

B. Samuelson, Proceedins of the National Academy of Science, U.S.A., Vol. 72, pages 2994–2980, 1975 and N. Kharasch and J. Fried, Biochemical Aspects of Prostaglandins and Thromboxanes, pages 133–154 and 189–198, (Academic Press), 1977 disclose that thromboxane $A_2$ is formed in the in vivo metabolic process of arachidonic acid and the thromboxane $A_2$ is a substance having strong actions of causing platelet aggregation and arterial contraction. The substance has therefore been presumed to induce thrombosis, transient ischemic heart attack and mycardial infarction. The compounds of formula (I) and their pharmaceutically acceptable acid addition salts which strongly inhibit platelet aggregation induced by arachidonic acid are useful for the prevention and treatment of thrombosis, transient ischemic heart attack and myocardial infraction.

The compounds of formula (I) and their pharmaceutically acceptable acid addition salts have vasodilating activity, and show strong blood pressure lowering activity and are useful for the prevention and treatment of hypertensive disorders.

Thus, the compounds of formula (I) and their pharmaceutically acceptable acid addition salts are useful as antithrombotic agents against thrombotic diseases, blood flow improvers against peripheral blood flow disorders, ischemic heart diseases, ischemic cerebral vessel disorders and senile demantia and as antihypertensive agents or vasodilators against hypertension.

According to this invention, there can be provided a pharmaceutical composition composed of an amount, effective against disorders of the blood circulating system, of a 2,6,7,8-substituted quinazoline represented by the following formula

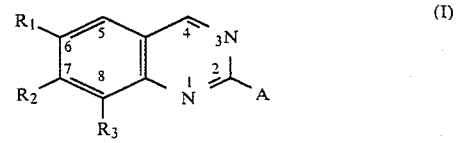

wherein $R_1$ and $R_2$ each represent a lower alkyl group, $R_2$ represents a lower alkoxy-carbonyl group, and A represents a lower alkyl group, or a phenyl or benzyl group which is unsubstituted or substituted by a substituent selected from the class consisting of halogen atoms, a trifluoromethyl group and lower alkyl groups, and a pharmaceutically acceptable diluent or carrier.

The pharmaceutical composition of this invention can be in various dosage forms, such as tablets, granules, powders, injectable preparations, and Ringer's solution.

Solid or liquid pharmaceutically acceptable diluents or carriers which can be utilized in these dosage forms are well known in the art, and can be used in this invention. Examples include talc, gum arabic, starch, magnesium stearate, lactose, coconut oil, corn oil, cotton seed oil, peanut oil, fish liver oil, oily esters, gelatin, glycerol, sorbic acid, physiological saline, cacao butter and other triglyceride antioxidants, wetting agents, dispersing agents, and emulsifiers.

The pharmaceutical composition of this invention may contain a suitable amount of the compound of formula (I) or its pharmaceutically acceptable acid addition salt. The amount of the active compound can be properly chosen depending upon the type of the active compound or the dosage form, and, for example, is about 0.1 to about 100% based on the weight of the composition.

The dosage of the composition of this invention can be varied widely depending upon the method of administration, the type and severity of a disorder to be treated, and, for example, the amount of the compound of formula (I) or its pharmaceutically acceptable acid addition salt is about 0.01 to about 300 mg/kg body/day.

The following Examples illustrate the present invention more specifically.

EXAMPLE 1

504 mg of ethyl 4-formyl-2,6-dimethyl-3-(o-chlorobenzoylamino)benzoate was dissolved in 50 ml of ethanol saturated with ammonia and the solution was left to stand overnight at room temperature. The solvent was evaporated, and the residue was separated and purified by silica gel column chromatography. Fractions eluted with diethyl ether/n-hexane (volume ratio 2:8) were collected and the solvent was evaporated. The residue was recrystallized from methanol/n-hexane to give 150 mg (yield 30%) of 2-(o-chlorophenyl)-7-ethoxycarbonyl-6,8-dimethylquinazoline having a melting point of 69.5° to 70.5° C.

Mass spectrum m/e: 342 (M+)

UV spectrum $\lambda_{max}^{EtOH}$: 250, 334 nm

NMR spectrum δ(ppm, measured in CDCl$_3$): 1.47 (3H, t, J=7 Hz), 2.53 (3H, s), 2.80 (3H, s), 4.51 (2H, q, J=7 Hz), 7.20–7.70 (4H, m), 7.80–8.05 (1H, m), 9.40 (1H, s).

Pharmacological Test Example 1

(1) Measurement of inhibitory effect on platelet aggregation:

Blood was drawn from ether-anesthetized rabbits (weighing 2.5 to 3.5 kg) through a canule inserted into the carotid artery. Immediately then, a 3.8% aqueous solution of sodium citrate was added to the collected blood in a volume of 1/10 of the volume of the blood after addition of the aqueous solution citrate solution. The blood was then centrifuged for 15 minutes at 150 G at room temperature to obtain plasma having platelet suspended therein as a supernatant.

An aliquot of 0.435 ml of platelet-rich plasma was put into the cell of an aggregometer adjusted to a temperature of 37° C. and a stirring speed of 1200 rpm. Then, a solution of a test compound in 2.5 μl of dimethyl sulfoxide was added so that the final concentration of the test compound became 30μ moles/liter or 10μ moles/liter, and the mixture was stirred for 3 minutes. An aqueous solution of arachidonic acid as a platelet aggregation inducing agent (the final concentration of arachidonic acid is 137μ moles/liter) was added, and with stirring, changes in absorbance were measured for 10 minutes.

The effect of platelet aggregation inhibition of the test compound was calculated as follows:

$$\text{Platelet inhibition (\%)} = \frac{\Delta C - \Delta S}{\Delta C} \times 100$$

ΔC: a change in absorbance in a control run,

ΔS: a change in absorbance when the test compound was added.

In the control run, 2.5 μl of dimethyl sulfoxide was added instead of the test compound.

The results are shown in Table I-1 below.

TABLE I-1

| Test compound | Final concentration of the test compound (μ moles/liter) | Platelet inhibition (%) |
|---|---|---|
| Compound of Example 1 | 30 | 100 (n = 4) |
| Compound of Example 1 | 10 | 100 (n = 3) |
| Compound of Example 1 | 3 | 100 (n = 1) |

(2) Blood pressure lowering activity

Rabbits (weighing 2.5 to 3 kg) were anesthetized by intravenously injecting an aqueous solution of sodium pentobarbital (35 mg/kg). The animals were fixed at the back, and the neck portions were mesially incised to expose the left common carotid artery. An arterial clamp was applied to the heart side to shut off the blood flow temporarily. The artery was incised to a small extent, and one end of a polyethylene tube filled with heparinized physiological saline was inserted thereinto toward the heart side and ligated. The other end of the tube was connected to a pressure transducer, and the blood pressure (average arterial pressure) was recorded on a recorder through an amplifier. The test compound was dissolved in 40% ethanol, and its concentration was adjusted so that the amount of administration became 0.1 ml/kg. The test compound was thus administered to the animals through a polyethylene tube inserted into the right carotid artery. The blood pressure lowering effects obtained are shown in Table I-2. Each of the blood pressure lowering effects was an average value of the results obtained by using at least three rabbits.

TABLE I-2

| Test compound | Dosage (i.v.) (μg/kg) | Pressure lowering effect (mmHg) |
|---|---|---|
| Compound of Example 1 | 10 | 12 |
| Compound of Example 1 | 30 | 22 |
| Compound of Example 1 | 100 | 49 |

EXAMPLE 2

Ethyl 4-formyl-2,6-dimethyl-3-benzoylaminobenzoate was used instead of the compound of formula (II) used in Example 1 and reacted with ammonia in the same way as in Example 1. The reaction product was chromatographed on a silica gel column in the same way as in Example 1. The solvent was evaporated, and the residue was recrystallized from diethyl ether/n-hexane to give 2-phenyl-7-ethoxycarbonyl-6,8-dimethylquinazoline having a melting point of 85° to 86° C. in a yield of 35% by weight.

Mass m/e: 306, 307 (M+) 277, 278 (base ion peak)

UV $\lambda_{max}^{EtOH}$ nm: 211.5, 267.7, 293$^{sh}$, 307$^{sh}$, 334$^{sh}$, 350$^{sh}$ IR $\nu_{max}^{KBr}$ cm$^{-1}$: 1730

Pharmacological Test Example 2

In the same way as in Pharmacological Test Example 1, the compound of this invention obtained in Example 2 was tested for inhibition of platelet aggregation and blood pressure lowering activity. The results are shown in Tables II-1 and II-2.

TABLE II-1

| Test compound | Final concentration of test compound (μ moles/liter) | Percent inhibition of platelet aggregation (%) |
|---|---|---|
| Compound of Example 2 | 30 | 100 (n = 2) |
| Compound of Example 2 | 10 | 100 (n = 1) |

TABLE II-2

| Test compound | Dosage (i.v.) (μg/kg) | Blood pressure lowering effect (mmHg) |
|---|---|---|
| Compound of Example 2 | 100 | 15 |

EXAMPLE 3

Instead of the compound of formula (II) used in Example 1, ethyl 4-formyl-2,6-dimethyl-3-(o-tolylamino)-benzoate was used and reacted with ammonia in the same way as in Example 1. The reaction product was chromatographed on a silica gel column in the same way as in Example 1. The solvent was evaporated, and the residue was recrystallized from ethanol/water to give 2-(o-methylphenyl)-7-ethoxycarbonyl-6,8-dimethylquinazoline having a melting point of 56° to 57° C. in a yield of 38%.

Mass m/e: 320 (M+; base ion peak) 291, 275

UV $\lambda_{max}^{EtOH}$ nm: 240 (shoulder), 261, 290 (shoulder) 330

IR $\nu_{max}^{KBr}$ cm$^{-1}$: 1720, 1260, 1200

NMR (CDCl$_3$)δ: 1.45 (3H, t, J=7 Hz), 2.51 (3H, s), 2.71 (3H, s), 2.77 (3H, s), 4.50 (2H, q, J=7 Hz), 7.20–7.50 (3H, m), 7.58 (1H, s), 8.0–8.20 (1H, m), 9.37 (1H, s).

Pharmacological Test Example 3

In the same way as in Pharmacological Test Example 1, the compound obtained in Example 3 was tested for inhibition of platelet aggregation and blood pressure lowering activity. The results are shown in Tables III-1 and III-2.

TABLE III-1

| Test compound | Final concentration of the test compound (μ moles/liter) | Inhibition of platelet aggregation (%) |
|---|---|---|
| Compound of Example 3 | 30 | 100 (n = 2) |
| Compound of Example 3 | 10 | 100 (n = 1) |

TABLE III-2

| Test compound | Dosage (i.v.) (μg/kg) | Blood pressure lowering effect (mmHg) |
|---|---|---|
| Compound of Example 3 | 100 | 20 |

EXAMPLE 4

Instead of the compound of formula (II) used in Example 1, ethyl 4-formyl-2,6-dimethyl-3-(o-fluorobenzoylamino)benzoate was used and reacted with ammonia in the same way as in Example 1. The reaction product was chromatographed on a silica gel column in the same way as in Example 1. The solvent was evaporated, and the residue was recrystallized from ethanol/water to give 2-(o-fluorophenyl)-7-ethoxycarbonyl-6,8-dimethylquinazoline having a melting point of 98° to 100° C. in a yield of 28%.

Mass m/e: 324 (M+), 295 (base ion peak)

UV $\lambda_{max}^{EtOH}$ nm: 260, 295 (shoulder), 330,

IR $\nu_{max}^{KBr}$ cm$^{-1}$: 1723, 1260, 1070,

NMR (CDCl$_3$)δ: 1.44 (3H, t, J=7 Hz), 2.50 (3H, s), 2.79 (3H, s), 4.50 (2H, q, J=7 Hz), 7.10–7.60 (3H, m), 7.58 (1H, s), 8.24 (1H, bt, J=7 Hz), 9.38 (1H, s).

Pharmacological Test Example 4

The compound obtained in Example 4 was tested for inhibition of platelet aggregation and blood pressure lowering activity in the same way as in Pharmacological Test Example 1.

The results are shown in Tables IV-1 and IV-2.

TABLE IV-1

| Test compound | Final concentration of the test compound (μ moles/liter) | Inhibition of platelet aggregation (%) |
|---|---|---|
| Compound of Example 4 | 3 | 100 (n = 3) |
| Compound of Example 4 | 1 | 100 (n = 1) |

TABLE IV-2

| Test compound | Dosage (i.v.) (μg/kg) | Blood pressure lowering effect (mmHg) |
|---|---|---|
| Compound of Example 4 | 100 | 32 |

EXAMPLE 5

Instead of the compound of formula (II) used in Example 1, ethyl 4-formyl-2,6-dimethyl-3-(o-trifluoromethylbenzoylamino)benzoate was used and reacted with ammonia in the same way as in Example 1. The reaction product was chromatographed on a silica gel column. The solvent was evaporated, and the residue was recrystallized from ethanol to give 2-(o-trifluoromethylphenyl)-7-ethoxycarbonyl-6,8-dimethylquinazoline having a melting point of 68° to 69° C. in a yield of 15%.

Mass m/e: 374 (M+), 345,

IR $\nu_{max}^{KBr}$ cm$^{-1}$: 1725, 1255, 1200, 1010.

NMR (TMS/CDCl$_3$), δ: 1.43 (3H, t), 2.50 (3H, s), 2.78 (3H, s), 4.50 (2H, q), 7.40–8.00 (5H, m), 9.37 (1H, s).

Pharmacological Test Example 5

The compound obtained in Example 5 was tested for inhibition of platelet aggregation and blood pressure lowering activity in the same way as in Pharmacological Test Example 1. The results are shown in Tables V-1 and V-2.

TABLE V-1

| Test compound | Final concentration of the test compound (μ moles/liter) | Inhibition of platelet aggregation (%) |
|---|---|---|
| Compound of Example 5 | 100 | 100 (n = 1) |

TABLE V-2

| Test compound | Dosage (i.v.) (μg/kg) | Blood pressure lowering effect (mmHg) |
|---|---|---|
| Compound of Example 5 | 100 | 25 |

EXAMPLE 6

Instead of the compound of formula (II) used in Example 1, ethyl 4-formyl-2,6-dimethyl-3-acetylaminobenzoate was used and reacted with ammonia in the same way as in Example 1. The reaction product was chromatographed on a silica gel column in the same way as in Example 1. The solvent was evaporated, and the residue was recrystallized from ethanol/water to give 2-methyl-7-ethoxycarbonyl-6,8-dimethylquinazoline having a melting point of 84° to 86° C. in a yield of 40%.

Pharmacological Test Example 6

The compound of this invention obtained in Example 6 was tested for inhibition of platelet aggregation and blood pressure lowering activity in the same way as in Pharmacological Test Example 1. The results are shown in Tables VI-1 and VI-2.

TABLE VI-1

| Test compound | Final concentration of the test compound (μ moles/liter) | Inhibition of platelet aggregation (%) |
|---|---|---|
| Compound of Example 6 | 100 | 100 (n = 1) |

TABLE VI-2

| Text compound | Dosage (i.v.) (μg/kg) | Blood pressure lowering effect (mmHg) |
|---|---|---|
| Compound of Example 6 | 100 | 12 |

EXAMPLE 7

Instead of the compound of formula (II) used in Example 1, ethyl 4-formyl-2,6-dimethyl-3-phenylacetylaminobenzoate was used and reacted in the same way as in Example 1. The product was chromatographed on a silica gel column in the same way as in Example 1. The solvent was evaporated, and the residue was recrystallized from ethanol/water to give 2-benzyl-7-ethoxycarbonyl-6,8-dimethylquinazoline having a melting point of 77° to 79° C. in a yield of 25%.

Mass m/e: 320 (M+, base ion peak), 291, 275,
UV $\lambda_{max}^{EtOH}$ nm: 237, 270 (shoulder), 330,
IR $\nu_{max}^{KBr}$ cm$^{-1}$: 1730, 1600, 1260, 1240,
NMR (DCDl$_3$)δ: 1.43 (3H, t, J=7 Hz), 2.46 (3H, s), 2.72 (3H, s), 4.44 (2H, s), 4.53, (2H, q, J=7 Hz), 7.10–7.50 (5H, m), 7.48 (1H, s), 9.19 (1H, s).

Pharmacological Test Example 7

The compound of this invention obtained in Example 7 was tested for inhibition of platelet aggregation and blood pressure lowering activity in the same way as in Pharmacological Test Example 1. The results are shown in Tables VII-1 and VII-2.

TABLE VII-1

| Test compound | Final concentration of the test compound (μ moles/liter) | Inhibition of platelet aggregation (%) |
|---|---|---|
| Compound of Example 7 | 100 | 100 (n = 3) |

TABLE VII-2

| Test compound | Dosage (i.v.) (μg/kg) | Blood pressure lowering effect (mmHg) |
|---|---|---|
| Compound of Example 7 | 100 | 18 |

What is claimed is:

1. A 2,6,7,8-substituted quinazoline represented by the following formula

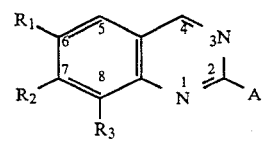

wherein R$_1$ and R$_3$ each represent a lower alkyl group, R$_2$ represents a lower alkoxy-carbonyl group, and A represents a lower alkyl group, or a phenyl or benzyl group which is unsubstituted or substituted by a substituent selected from the class consisting of halogen atoms, a trifluoromethyl group and lower alkyl groups, or its pharmaceutically acceptable acid addition salt.

2. A 2,6,7,8-substituted quinazoline represented by the following formula

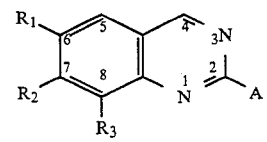

wherein R$_1$ and R$_3$ each represent an alkyl group having 1 to 3 carbon atoms, R$_2$ represents an alkoxy-carbonyl group with the alkyl moiety having 1 to 3 carbon atoms, and A represents an alkyl group having 1 to 3 carbon atoms, or a phenyl or benzyl group which is unsubstituted or substituted by a substituent selected from the class consisting of halogen atoms, a trifluoromethyl group and alkyl groups having 1 to 3 carbon atoms or its pharmaceutically acceptable acid addition salt.

3. The compound of claim 2 wherein $R_1$ and $R_3$ each represent a methyl group and $R_2$ represents an ethoxycarbonyl group.

4. The compound of claim 1 wherein the pharmaceutically acceptable acid addition salt is an acid addition salt of hydrochloric acid, sulfuric acid, hydrobromic acid, oxalic acid, maleic acid or malic acid.

5. The compound of claim 1 which is selected from the group consisting of 2-(o-chlorophenyl)-7-ethoxycarbonyl-6,8-dimethylquinazoline, 2-phenyl-7-ethoxycarbonyl-6,8-dimethylquinazoline, 2-(o-methylphenyl)-7-ethoxycarbonyl-6,8-dimethylquinazoline, 2-(o-fluorophenyl)-7-ethoxycarbonyl-6,8-dimethylquinazoline, 2-(o-trifluoromethylphenyl)-7-ethoxycarbonyl-6,8-dimethylquinazoline, 2-methyl-7-ethoxycarbonyl-6,8-dimethylquinazoline, and 2-benzyl-7-ethoxycarbonyl-6,8-dimethylquinazoline, or the pharmaceutically acceptable acid addition salts thereof.

6. A pharmaceutical composition composed of a pharmaceutically effective amount of a 2,6,7,8-substituted quinazoline represented by the following formula

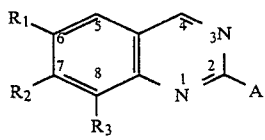

wherein $R_1$ and $R_3$ each represents a lower alkyl group, $R_2$ represents a lower alkoxy-carbonyl group, and A represents a lower alkyl group, or a phenyl or benzyl group which is unsubstituted or substituted by a substituent selected from the class consisting of halogen atoms, a trifluoromethyl group and lower alkyl groups, or its pharmaceutically acceptable acid addition salt, and a pharmaceutically acceptable diluent or carrier.

7. The pharmaceutical composition of claim 6 wherein $R_1$ and $R_3$ each represent an alkyl group having 1 to 3 carbon atoms, $R_2$ represents an alkoxycarbonyl group with the alkyl moiety having 1 to 3 carbon atoms, and A represents an alkyl group having 1 to 3 carbon atoms or a phenyl or benzyl group which is unsubstituted or substituted by a substituent selected from the class consisting of halogen atoms, a trifluoromethyl group and alkyl groups having 1 to 3 carbon atoms.

8. The pharmaceutical composition of claim 6 or 7 wherein $R_1$ and $R_3$ each represent a methyl group, and $R_2$ represents an ethoxycarbonyl group.

9. The pharmaceutical composition of claim 6 which contains at least 0.1% by weight of the 2,6,7,8-substituted quinazoline compound.

10. The pharmaceutical composition of claim 6 wherein the 2,6,7,8-substituted quinazoline compound is selected from the group consisting of 2-(o-chlorophenyl)-7-ethoxycarbonyl-6,8-dimethylquinazoline, 2-phenyl-7-ethoxycarbonyl-6,8-dimethylquinazoline, 2-(o-methylphenyl)-7-ethoxycarbonyl-6,8-dimethylquinazoline, 2-(o-fluorophenyl)-7-ethoxycarbonyl-6,8-dimethylquinazoline, 2-(o-trifluoromethylphenyl)-7-ethoxycarbonyl-6,8-dimethylquinazoline, 2-methyl-7-ethoxycarbonyl-6,8-dimethylquinazoline, and 2-benzyl-7-ethoxycarbonyl-6,8-dimethylquinazoline, or the pharmaceutically acceptable acid addition salts thereof.

* * * * *